(12) United States Patent
Hua et al.

(10) Patent No.: US 10,023,542 B2
(45) Date of Patent: Jul. 17, 2018

(54) IBRUTINIB INTERMEDIATE COMPOUNDS, PREPARATION METHODS AND USES THEREOF

(71) Applicant: Zhejiang Jiuzhou Pharma science&technology Co., Ltd, Hangzhou (CN)

(72) Inventors: Yunyu Hua, Taizhou (CN); Xianyi Zhang, Taizhou (CN); Hongjun Gao, Taizhou (CN); Yuanqiang Li, Taizhou (CN); Daqing Che, Taizhou (CN)

(73) Assignee: Zhejiang Jiuzhou Pharmaceuticals Co., Ltd, Taizhou Zhenjiang (CN)

( * ) Notice: Subject to any disclaimer, the term of this patent is extended or adjusted under 35 U.S.C. 154(b) by 0 days.

(21) Appl. No.: 15/321,750

(22) PCT Filed: Apr. 21, 2015

(86) PCT No.: PCT/CN2015/077039
§ 371 (c)(1),
(2) Date: Dec. 23, 2016

(87) PCT Pub. No.: WO2016/000476
PCT Pub. Date: Jan. 7, 2016

(65) Prior Publication Data
US 2017/0137386 A1    May 18, 2017

(30) Foreign Application Priority Data

Jul. 3, 2014    (CN) .......................... 2014 1 0313610

(51) Int. Cl.
*C07D 239/26*    (2006.01)
*C07D 487/04*    (2006.01)

(52) U.S. Cl.
CPC ......... *C07D 239/26* (2013.01); *C07D 487/04* (2013.01)

(58) Field of Classification Search
CPC .......................... C07D 239/30; C07D 487/04
See application file for complete search history.

(56) References Cited

U.S. PATENT DOCUMENTS

| | | | |
|---|---|---|---|
| 7,514,444 B2 | 4/2009 | Honigberg et al. | |
| 2017/0137386 A1* | 5/2017 | Hua | C07D 239/26 |
| 2017/0313683 A1* | 11/2017 | Wang | C07D 401/14 |
| 2017/0327504 A1* | 11/2017 | Rose | C07D 487/04 |

FOREIGN PATENT DOCUMENTS

| | | | |
|---|---|---|---|
| CN | 103626774 A | | 3/2014 |
| CN | 104844573 A | * | 8/2015 |
| CN | 105622613 A | * | 6/2016 |
| WO | WO2013157022 A1 | | 10/2013 |
| WO | WO-2016112637 A1 | * | 7/2016 |

OTHER PUBLICATIONS

CAS Abstract CN 104844573 (2015).*
English abstract; Chinese Application No. CN 103626774.

* cited by examiner

*Primary Examiner* — Alexander R Pagano

(57) ABSTRACT

The present invention relates to the technical field of ibrutinib, particularly to the technical field of ibrutinib intermediate compounds and preparation methods thereof. The intermediate compounds are represented by formula A, wherein, the dotted line represents a double bond or a single bond between carbon and oxygen.

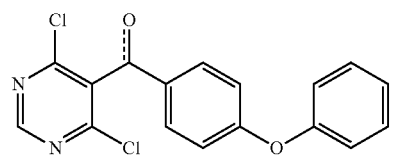

A

9 Claims, No Drawings

IBRUTINIB INTERMEDIATE COMPOUNDS, PREPARATION METHODS AND USES THEREOF

This application is a national stage application based on PCT/CN2015/077039, filed on Apr. 21, 2015, which claims the priority of China Patent Application No. 201410313610.7, filed with the Patent Office of China on Jul. 3, 2014, titled "Ibrutinib intermediate compounds, preparation methods and uses thereof", the contents of which are incorporated herein by reference in its entirety.

FIELD OF THE INVENTION

The present invention relates to the technical field of ibrutinib, particularly to the technical field of ibrutinib intermediate compounds and preparation methods thereof.

BACKGROUND OF THE INVENTION

Ibrutinib has the following structure, with a chemical name of 1-[(3R)-3-[4-Amino-3-(4-phenoxyphenyl)-1H-pyrazolo[3,4-d]pyrimidin-1-yl]piperidin-1-yl]prop-2-en-1-one

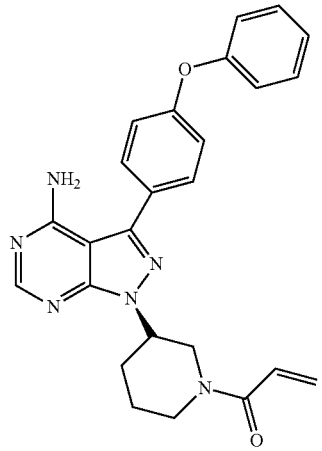

Ibrutinib is the first in class of an oral Bruton's tyrosine kinase (BTK) inhibitor for the treatment of chronic lymphocytic leukemia (CLL) and is one of the first medicines to file for FDA approval via the new Breakthrough Therapy Designation pathway. Ibrutinib forms a covalent bond with a cysteine residue (Cys-481), leading to irreversible inhibition of BTK, thus effectively blocking the transfer of cancer cell from B-cell to lymphoid tissue where is benefit for the growth of tumor.

The intermediate compound having the following structure is employed to synthesize ibrutinib.

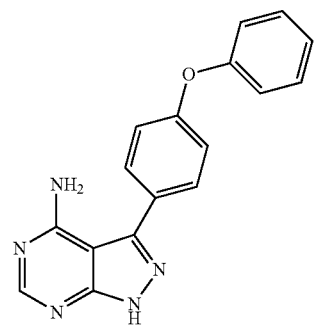

The compound of formula VI can be used to produce ibrutinib according to the method disclosed in America U.S. Pat. No. 7,514,444, and its synthesis route is depicted as below:

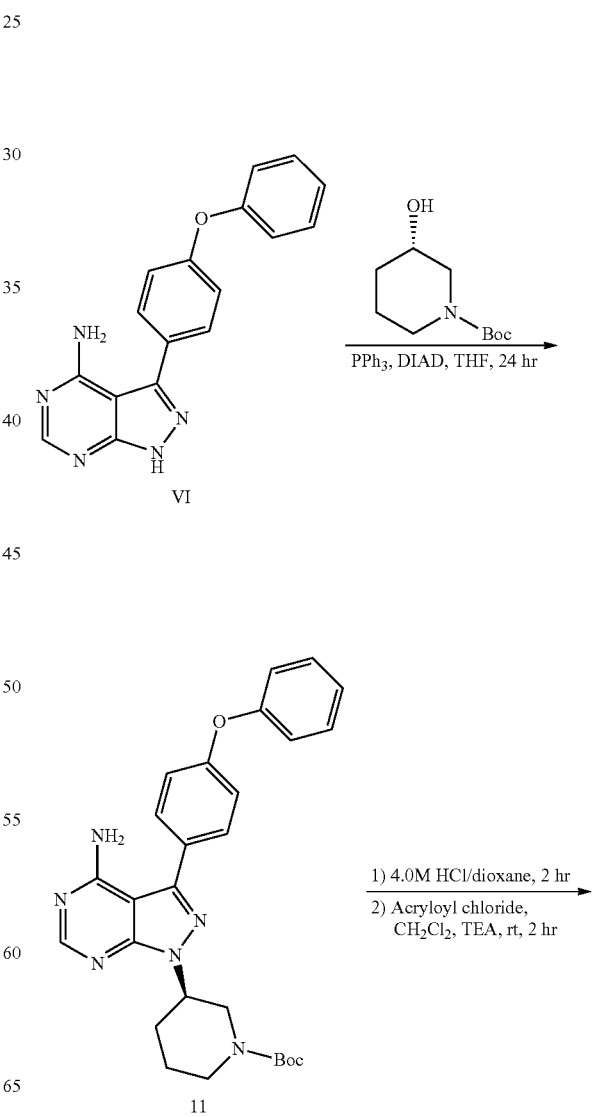

3
-continued

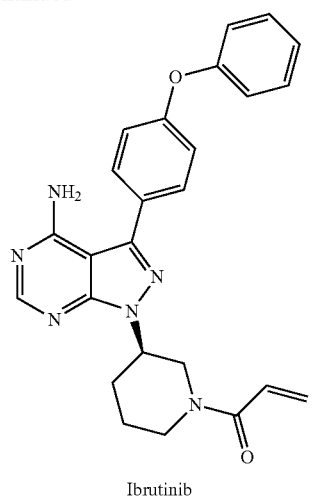
Ibrutinib

The current methods for preparing the compound of formula VI are confined to two routes published in America U.S. Pat. No. 7,514,444, which can be represented by the following two routes:

Route 1:

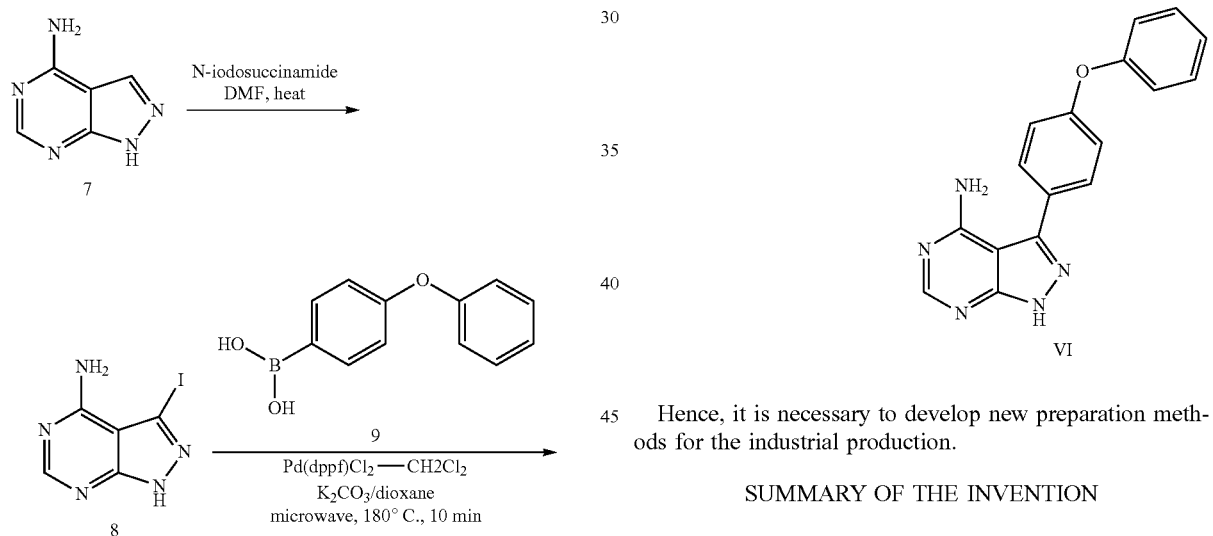

4
Route 2:

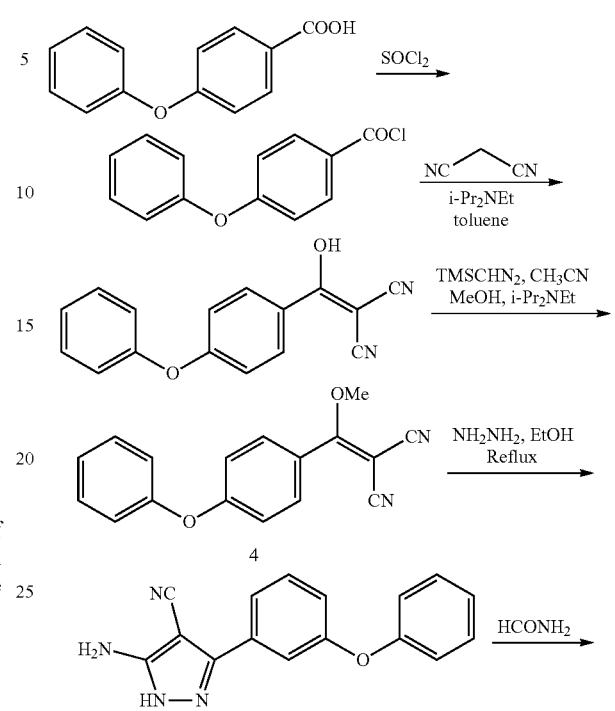

Hence, it is necessary to develop new preparation methods for the industrial production.

SUMMARY OF THE INVENTION

To provide a new method for preparing the compound of formula VI, the present invention adopts the following technical proposal:

A compound of formula A has the following structure:

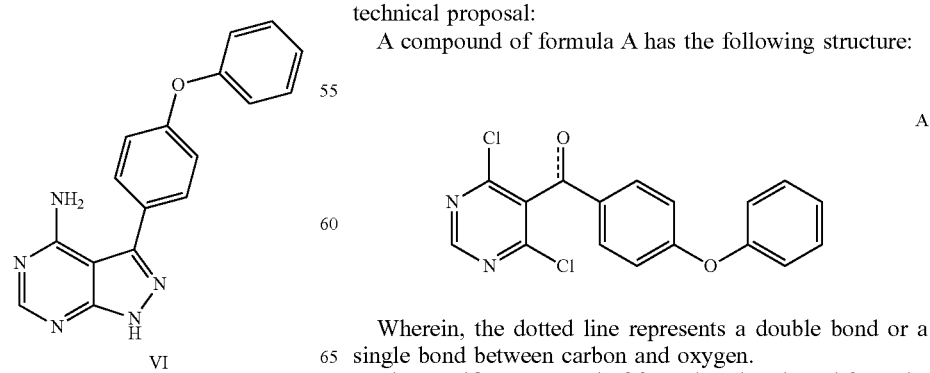

Wherein, the dotted line represents a double bond or a single bond between carbon and oxygen.

The specific compound of formula A is selected from the followings:

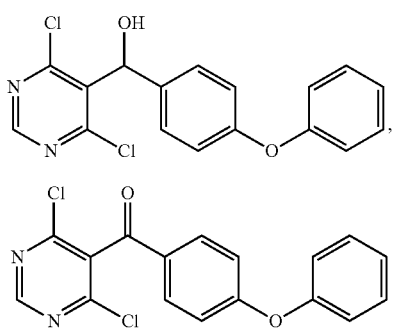

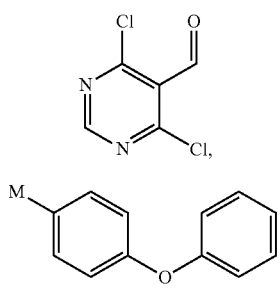

The following compound of formula I and the compound of formula II undergo nucleophilic addition reaction to produce the compound of formula III

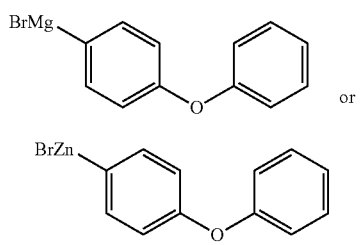

Wherein, M is Li, MgX or ZnX; X is Br or Cl, Preferably, X is Br.

The molar ratio of the compound of formula II to the compound of formula I is (1-2.5) to 1.

The preferred compound of formula has the following structures:

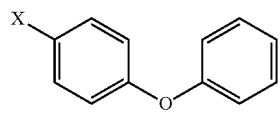

When M is MgX or ZnX, the compound of formula II was obtained by reacting the Mg or Zn with the compound of formula 2 in the present of initiator, the initiator is dibromoethane or I; the compound of formula II can be produced by the metal exchange reaction of the compound of formula 2 with organic metal salt, the preferred organic metal salt is isopropylmagnesium chloride or i-PrMgCl.LiCl.

When M is Li, the compound of formula II can be synthesized by reacting diphenyl ether with lithium alkylide, the preferred lithium alkylide is $C_{1-6}$ lithium alkylide.

The molar ratio of diphenyl ether to lithium alkylide is 1:(1.0-5.0).

The compound of formula III was subjected to oxidation reaction to afford the compound of formula IV, oxidizing agent utilized can be selected from $CrO_3$, $KMnO_4$, TEMPO (2,2,6,6-tetramethyl-4-piperidinooxy), TMPO (2,2,6,6-tetramethylpiperidine)/[O], DMP (Dess-Martin Periodinane), IBX (2-iodoxybenzoicacid), dimethyl sulfoxide/triethylamine/oxalyl chloride (Swern Oxidation), active $MnO_2$ or $MnO_2$.

Wherein [O] can be NCS (N-chlorosuccinimide), NBS (N-bromosuccinimide), NIS (N-iodosuccinimide), IBX, 1,3-dibromo-5,5-dimethyl hydantoin, hydrogen peroxide, NaClO or $Ca(ClO)_2$.

The preferred oxidizing agent can be selected from TEMPO/NBS, TEMPO/NaClO.

The present invention provides a compound of formula V having the following structure:

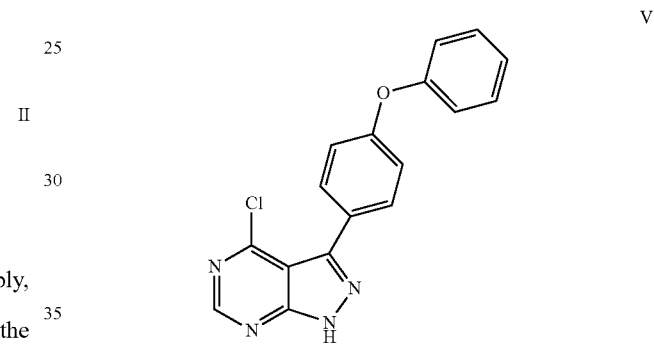

The compound of formula V is obtained by reacting the compound of formula IV with hydrazine hydrate.

The molar ratio of the compound of formula IV to hydrazine hydrate is 1: (1.0-5.0).

The preferred hydrazine hydrate is dissolved in water to form an aqueous solution.

The concentration of hydrazine hydrate aqueous solution is 10-95%.

The preferred concentration is 85%.

The reaction further comprises the step of the addition of diisopropylethylamine.

Further, the compound of formula V was reacted with ammonia to produce the compound of formula VI.

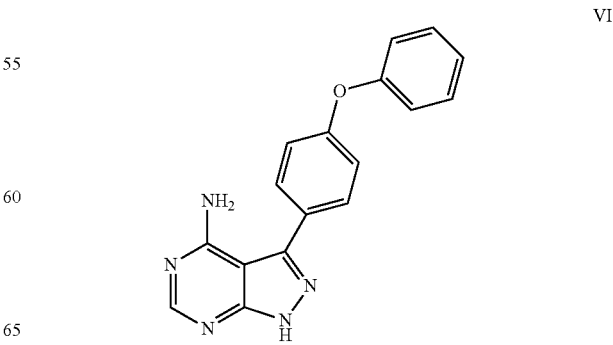

DETAILED EMBODIMENTS

The preferred ammonia is ammonia aqueous solution or ammonia/organic solvent, the organic solvent is selected from methanol, ethanol, isopropanol, tetrahydrofuran, toluene or a mixture of any two or more thereof.

The ammonia/organic solvent can be formed by bubbling ammonia gas into organic solvent directly.

The preferred ammonia/organic solvent is ammonia/toluene

In order to better understand the present invention, it is illustrated in detail by the following examples. However, it should be understood that these descriptions are not to limit the claims of the present invention.

Example 1: The Preparation of the Compound of Formula III

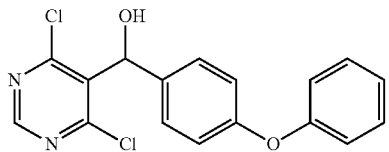

III

To a 250 mL flask was added magnesium wire (1.28 g, 53.5 mmol) and magnetic stir bar. The original atmosphere was displaced with $N_2$. 4-bromodiphenyl ether (1.10 g, 4.42 mmol), 15 mL of anhydrous tetrahydrofuran were injected into the flask. A grain of iodine was added for activation under $N_2$ flow, subsequently, a solution of 4-bromodiphenyl ether in anhydrous THF (10.00 g/35 ml) was added dropwise at 40~45° C. After the completion of the addition, the mixture was heated under reflux for 1 h, and then cooled naturally, stored for next step. To a 250 ml reaction flask was added 4,6-dichloro-5-2-pyrimidine-carboxaldehyde (7.1 g, 40.5 mmol) and 45 ml of anhydrous THF. The original atmosphere was displaced with $N_2$. To the mixture of 4,6-dichloro-5-2-pyrimidinecarboxaldehyde and THF was added the obtained Grignard reagent after cooling to −78° C., and the temperature was maintained at −80° C. to −75° C. After addition, it was maintained at this temperature for 30 min and then heated naturally to 20-25° C. with stirring for another 30 min. the reaction was quenched by adding dropwise 50 ml water. 100 ml DCM was added and the mixture was adjusted to pH 5-6 with concentrated hydrochloric acid. The organic layer was separated and the aqueous layer was extracted with 100 ml DCM. The combined organic layers were washed with saturated 100 ml $NaHCO_3$ and 100 ml saturated brine successively, and dried over $Na_2SO_4$. The solvent was removed to provide 13.38 g product with a yield of 95.2%.

HNMR: δ8.78 (1H, s); 7.36 (2H, t); 7.26 (2H, d); 7.12 (1H, t); 7.02 (3H, m); 6.54 (1H, d); 3.12 (1H, d)

LC-MS(+ESI): 347.0039

Example 2: The Preparation of the Compound of Formula III

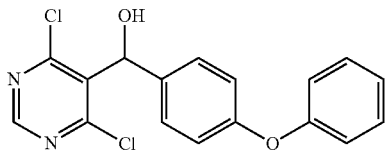

III

To a 250 mL flask was added magnesium wire (1.28 g, 53.5 mmol) and magnetic stir bar. The original atmosphere was displaced with $N_2$. Dibromoethane was added for activation. A solution of 4-bromodiphenyl ether (11.1 g, 44.6 mmol) and anhydrous tetrahydrofuran 50 ml were injected into the flask at 40-45° C. After addition, the mixture was heated under reflux for 1 h, cooled naturally and then stored for next step. To another 250 ml flask was added 4,6-dichloro-5-2-pyrimidinecarboxaldehyde (7.1 g, 40.5 mmol) and 45 ml THF. The original atmosphere was displaced with $N_2$. To the 4,6-dichloro-5-pyrimidinecarboxaldehyde was added the obtained Grignard reagent after cooling to −78° C., and the temperature was maintained at −80° C. to −75° C. After addition, it was maintained at this temperature for 30 min and then heated naturally to 20-25° C. with stirring for another 30 min. the reaction was quenched by adding dropwise 50 ml water. 100 ml DCM was added and the mixture was adjusted to pH 5-6 with concentrated hydrochloric acid. The organic layer was separated and the aqueous layer was extracted with 100 ml DCM. The combined organic layers were washed with saturated 100 ml $NaHCO_3$ and 100 ml saturated brine successively, and dried over $Na_2SO_4$. The solvent was removed to provide 12.69 g product with a yield of 90.3%.

Example 3: The Preparation of the Compound of Formula III

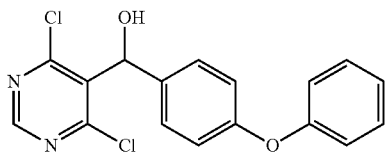

III

To the solution of diphenyl ether in tetrahydrofuran (8.5 g, 50 mmol)/50 ml was added a solution of n-butyllithium in n-hexane (32 ml, 50 mmol, 1.6M) at below −75° C. under the protection of nitrogen. The reaction was stirred for 2 h, then 4,6-dichloro-5-pyrimidinecarboxaldehyde (8.8 g, 50 mmol) was added. The reaction mixture was maintained at −75° C. for 5 h. after the completion of the reaction, it was quenched with water and tetrahydrofuran. The reaction mixture was extracted with dichloromethane. The residue was purified by chromatography over silica gel to afford 14.35 g product with a yield of 82.7%.

Example 4: The Preparation of the Compound of Formula III

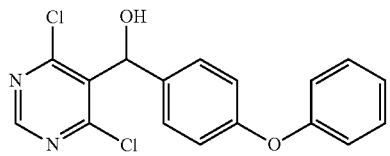

III

To the solution of 4-bromophenylphenylether and tetrahydrofuran (10 g, 40.2 mmol)/50 ml was added dropwise i-PrMgCl—LiCl (41 mL, 1.1 M in THF, 45.1 mmol) at −70° C. under the protection of nitrogen. After addition, the reaction mixture was stirred at −70° C. for 4 h, then 4,6-dichloro-5-pyrimidinecarboxaldehyde was added. The reaction mixture was stirred at below −70° C. for 5 h. after the completion of the reaction, it was quenched with 50 ml of saturated aqueous ammonium chloride. The reaction mixture was extracted with dichloromethane and then the combined dichloromethane layers were concentrated. The residue was purified chromatography over silica gel to afford 11.88 g product, with a yield of 85.6%.

Example 5: The Preparation of the Compound of Formula IV

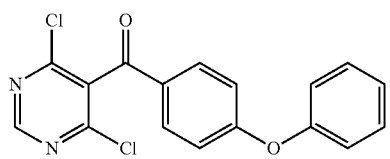

IV

NaHCO$_3$ (0.49 g, 4.62 mmol), 5 ml deionized water and magnetic stir bar were charged into a flask and then was stirred to form a clear solution. 10 ml dichloromethane, the compound of formula III (1.00 g, 2.9 mmol), TEMPO (0.0226 g, 0.15 mmol) and NBS (1.03 g, 5.79 mmol) were added at below 25° C., after addition, the mixture was stirred for 1 h. Upon completion, the layers were separated, and organic layer was purified by chromatography over silica gel to afford 0.879 g product, with a yield of 87.9%.

HNMR: δ 8.89 (1H, s); 7.78 (2H, d); 7.42 (2H, t); 7.26 (1H, t); 7.12 (2H, d); 7.03 (2H, d).

LC-MS (+ESI): 345.0193.

Example 6: The Preparation of the Compound of Formula IV

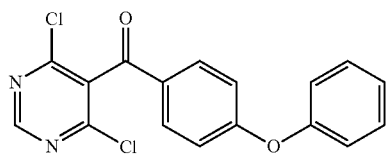

IV 10 ml of dichloromethane, the compound of formula III (1.00 g, 2.9 mmol) were charged into a flask and then was stirred to form a clear solution. TEMPO (0.47 g, 3.0 mmol) was added in batches at below 25° C. After the addition, the mixture was stirred at same temperature. Upon completion, it was washed with water. The layers were separated. The solvent was removed and the resulting residue was purified by chromatography over silica gel to afford 0.72 g product, with a yield of 72.0%.

Example 7: The Preparation of the Compound of Formula IV

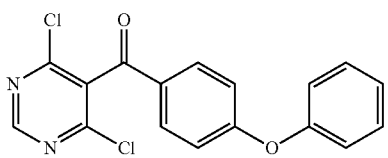

IV

A mixture of the compound of formula III (1.5 g, 4.3 mmol), acetonitrile 50 ml and KMnO$_4$ (4.2 g, 27 mmol) was stirred at 0-105° C. for 7 h. Upon completion, the resulting mixture was filtrated, concentrated, and then purified by chromatography over silica gel to afford a product, with a yield of 80.5%.

Example 8: The Preparation of the Compound of Formula IV

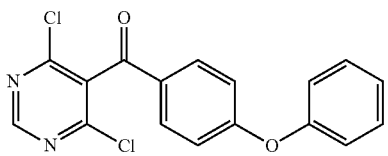

IV

A mixture of the compound of formula IV (1.5 g, 4.3 mmol), anhydrous acetone 50 ml and CrO$_3$ (1.51 g, 15.1 mmol) were stirred at 0-105° C. for 7 h. upon completion, isopropanol (5 ml) was added with stirring for 1 h. To the mixture was added 5% aqueous sodium bicarbonate (50 ml) with stirring for 5 min, was extracted with dichloromethane, concentrated and then purified by chromatography over silica gel to afford a product, with a yield of 76.2%.

Example 9: The Preparation of the Compound of Formula IV

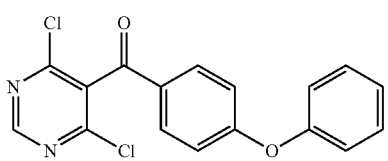

IV

KBr (0.863 g, 0.725 mmol), 5 ml deionized water and magnetic stir bar were charged into a flask and then was stirred to form a clear solution. 10 ml dichloromethane, the compound of formula III (1.00 g, 2.9 mmol), TEMPO (0.0226 g, 0.15 mmol) and NaClO (4 g, 5.8 mmol) were added at below 25° C. and stirred for 1 h. Upon completion, the layers were separated, and organic layer was purified by chromatography over silica gel to afford 0.964 g product, with a yield of 96.4%.

Example 10: The Preparation of the Compound of Formula V

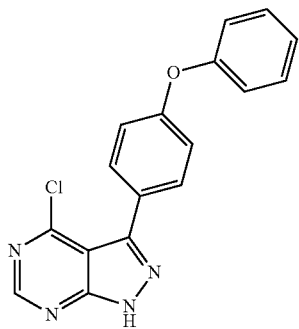

V

To a flask was added the compound of formula IV (9.50 g, 27.5 mmol), DIPEA (7.11 g, 55.1 mmol) and 180 ml THF and then cooled to 0-5° C. under the protection of $N_2$. 1.70 g hydrazine hydrate with the concentration of 85% was added dropwise at below 5° C. After the dropping, the mixture was warmed naturally to 20-25° C. and then stirred for 4 h. Upon completion, it was purified by chromatography over silica gel to afford 8.2 g product, with a yield of 92.7%.

HNMR: δ11.8 (1H, s); 8.8 (1H, s); 7.7 (2H, d); 7.4 (2H, t); 7.2 (1H, t); 7.1 (5H, m)

LC-MS (+ESI): 323.0698

Example 11: The Preparation of the Compound of Formula V

To a flask was added the compound of formula IV (9.50 g, 27.5 mmol), DIPEA (7.11 g, 55.1 mmol) and 180 ml THF and then cooled to 0-5° C. under the protection of $N_2$. Hydrazine hydrate (1.5 g, 30 mmol) was added at below 5° C. After the addition, the mixture was warmed naturally to 20-25° C. and then stirred for 4 h. Upon completion, it was purified by chromatography over silica gel to afford 7.32 g product, with a yield of 82.7%.

Example 12: The Preparation of the Compound of Formula V

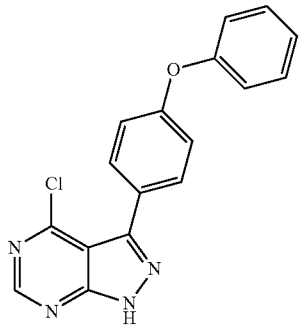

V

To a flask was added the compound of formula IV (9.50 g, 27.5 mmol) and 180 ml THF and then cooled to 0-5° C. under the protection of $N_2$. 1.70 g hydrazine hydrate (1.5 g, 30 mmol) with the concentration of 85% was added at below 5° C. After the addition, the mixture was warmed naturally to 20-25° C. and then stirred for 4 h. Upon completion, it was purified by chromatography over silica gel to afford 6.99 g product, with a yield of 78.9%.

Example 13: The Preparation of the Compound of Formula V

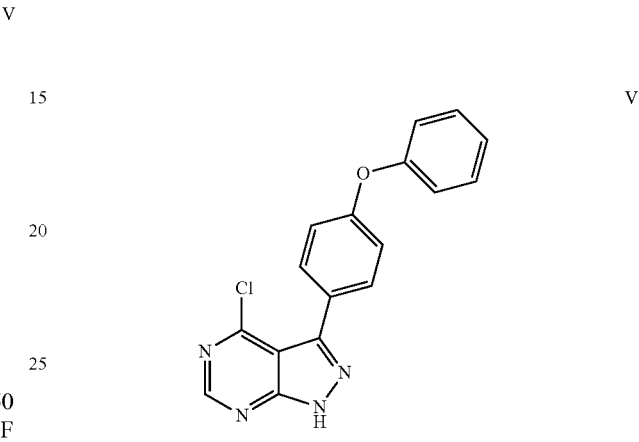

V

To a flask was added the compound of formula IV (9.50 g, 27.5 mmol), DIPEA (7.11 g, 55.1 mmol) and 180 ml THF and then cooled to 0-5° C. under the protection of $N_2$. 5 g hydrazine hydrate (1.5 g, 30 mmol) with the concentration of 40% was added at below 5° C. After the addition, the mixture was warmed naturally to 20-25° C. and then stirred for 4 h. Upon completion, it was purified by chromatography over silica gel to afford 7.46 g product, with a yield of 84.3%.

Example 14: The Preparation of the Compound of Formula VI

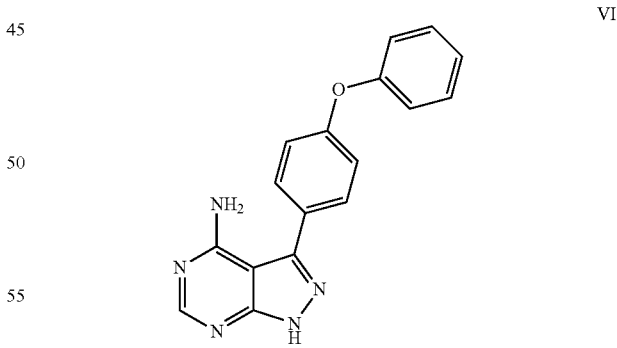

VI

To a flask was added the compound of formula V (1.00 g, 3.1 mmol) and 10 ml of a solution of ammonia in methanol with a concentration of 10%, heated under reflux and then stirred for 12 h. Upon completion, the resulting mixture was purified by chromatography over silica gel to afford 0.89 g product, with a yield of 89.2%.

HNMR: δ 13.5 (1H, s); 8.2 (1H, s); 7.6 (2H, t); 7.4 (2H, t); 7.2 (1H, t); 7.1 (4H, m)

LC-MS (+ESI): 304.0938.

All the documents mentioned in the present invention are incorporated herein by reference, as if each of them is individually incorporated. Further, it would be appreciated that the foregoing description presents specific embodiments and generic principles of the invention. Having read the above described teaching of the invention, one skilled in the art could make various changes or modifications to the invention without departing from the spirit and scope of the invention. These equivalents would still be within the scope of the invention.

The invention claimed is:

1. A compound of formula A having the following structure:

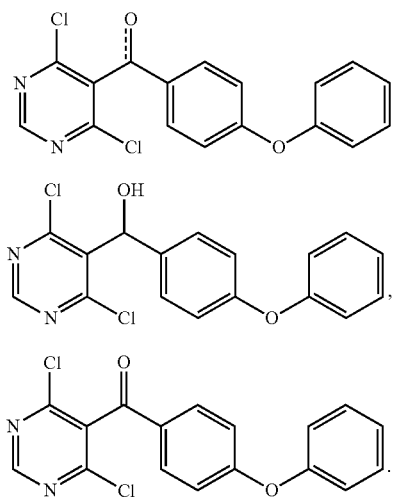

wherein, the dotted line represents a double bond with structure of formula IV of the compound or a single bond between carbon and oxygen with structure of formula III of the compound.

2. A process for preparing the compound of formula III, comprising the compound of formula I and the compound of formula II undergoing nucleophilic addition reaction,

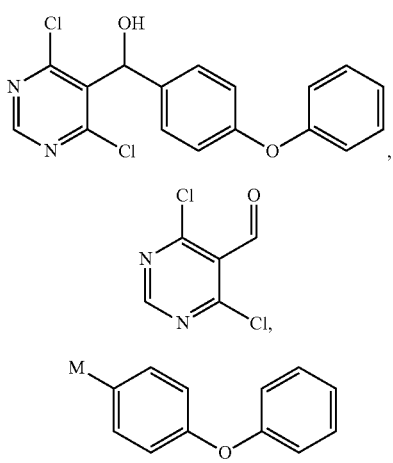

wherein, M is Li, MgX or ZnX; X is Br or Cl.

3. A process for preparing the compound of formula IV, comprising subjecting the compound of formula III to oxidation reaction,

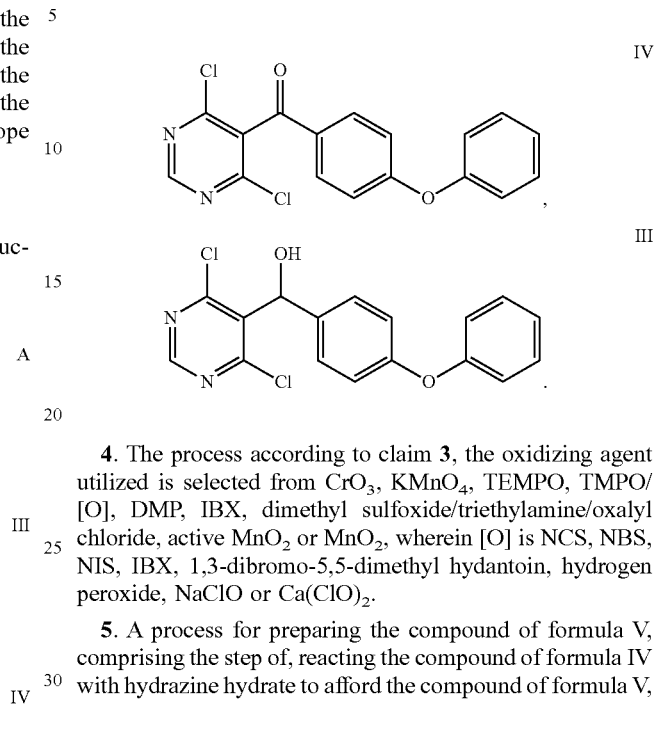

4. The process according to claim 3, the oxidizing agent utilized is selected from CrO$_3$, KMnO$_4$, TEMPO, TMPO/[O], DMP, IBX, dimethyl sulfoxide/triethylamine/oxalyl chloride, active MnO$_2$ or MnO$_2$, wherein [O] is NCS, NBS, NIS, IBX, 1,3-dibromo-5,5-dimethyl hydantoin, hydrogen peroxide, NaClO or Ca(ClO)$_2$.

5. A process for preparing the compound of formula V, comprising the step of, reacting the compound of formula IV with hydrazine hydrate to afford the compound of formula V,

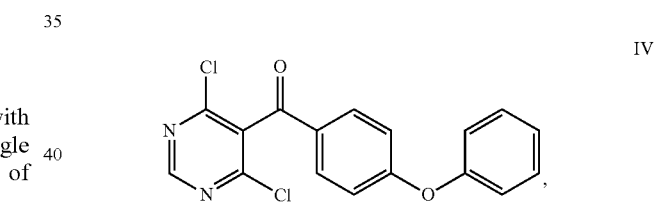

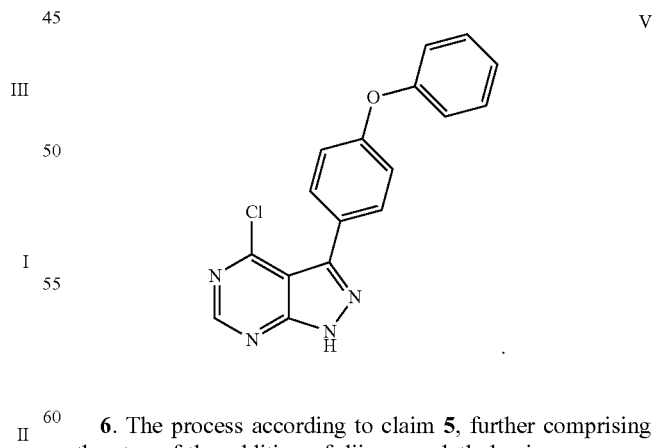

6. The process according to claim 5, further comprising the step of the addition of diisopropylethylamine.

7. A process for preparing the compound of formula VI, comprising the step of, reacting the compound of formula IV with hydrazine hydrate to afford the compound of formula V, further reacted with ammonia to produce the compound of formula VI,

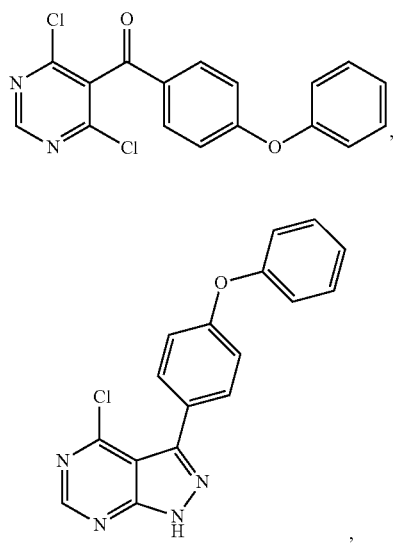
IV
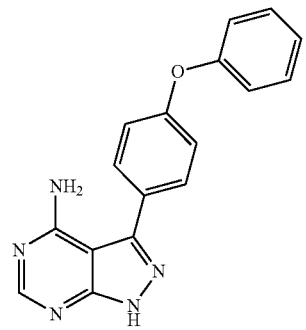
VI
V
8. The process according to claim 7, the ammonia is ammonia aqueous solution or ammonia/organic solvent, the organic solvent is selected from methanol, ethanol, isopropanol, tetrahydrofuran, toluene or a mixture of any two or more thereof.
9. The process according to claim 8, the ammonia/organic solvent is ammonia/toluene.
* * * * *